US00PP29207P2

(12) United States Plant Patent
Hansen

(10) Patent No.: US PP29,207 P2
(45) Date of Patent: Apr. 3, 2018

(54) ***HEUCHERA* PLANT NAMED 'SILVER GUMDROP'**

(50) Latin Name: ***Heuchera* hybrid**
Varietal Denomination: Silver Gumdrop

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,027

(22) Filed: Nov. 21, 2016

(51) Int. Cl.
*A01H 5/12* (2018.01)

(52) U.S. Cl.
USPC ..... Plt./440

(58) Field of Classification Search
USPC ..... Plt./440
CPC . A01H 5/02; A01H 5/12; A01H 5/025; A01H 5/00
See application file for complete search history.

(56) References Cited

PUBLICATIONS

Hosta Choice Gardens *Heuchera* & Heucherella Availability 2016 retrievd on Oct. 31, 2016, retrieved from the Internet at https://www.hostachoicegardens.com/images/Heuchera_and_Heucherella_2016_Availability.pdf 2 pp. (Year: 2016).*

* cited by examiner

*Primary Examiner* — June Hwu

(57) ABSTRACT

The new and distinct hybrid of *Heuchera* plant named 'Silver Gumdrop' with small cordate leaf blades of intensely silver coloring and very thin dark green surrounding the veins. Foliage has rounded apices and shallowly-cleft lobe and develops a complementary rosy blush by mid-summer. The burgundy-colored panicle has short branches producing vibrant pink flowers from early to late summer. The new plant is vigorous and compact in habit.

1 Drawing Sheet

Botanical denomination: *Heuchera* hybrid.
Variety denomination: 'Silver Gumdrop'.

BACKGROUND OF THE INVENTION

The present invention relates to a new and distinct cultivar of Coral Bells in the Saxifragaceae family and given the cultivar name of 'Silver Gumdrop'. *Heuchera* 'Silver Gumdrop' was hybridized by the inventor on Apr. 22, 2013 at a wholesale perennial nursery in Zeeland, Mich., USA and initially assigned the breeder code 13-802-1. The seed or female parent was a proprietary unreleased hybrid known only by the breeder code 12-490-01 (not patented) and the pollen or male parent was a proprietary unreleased hybrid known only by the breeder code K11-52-15 (not patented). The female parent consists of genes from 'Tiramisu' U.S. Plant Pat. No. 20,429, 'Mocha' U.S. Plant Pat. No. 18,386, 'Mocha Mint' (not patented) and 'Stainless Steel' U.S. Plant Pat. No. 23,349, and the male parent consist of genes from 'Milan' U.S. Plant Pat. No. 21,682 and 'Mocha Mint'.

The new invention has a mixture of *Heuchera americana, H. brizoides, H. micrantha* and *H. villosa* in the pedigree.

*Heuchera* 'Silver Gumdrop' was first selected in the fall of 2013 and passed final evaluation in the fall of 2014 from among thousands of other seedlings from the same cross and hundreds of other crosses. *Heuchera* 'Silver Gumdrop' has been asexually propagated by division at the same nursery in Zeeland, Mich. in 2014 and by careful shoot tip tissue culture propagation, and the resultant plants have remained stable and continued to exhibit the same characteristics as the original plant for multiple generations.

No plants of *Heuchera* 'Silver Gumdrop' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

In comparison to the ancestor cultivars on the female side, 'Tiramisu', *Heuchera* 'Silver Gumdrop' does not have the butterscotch leaf coloration that also develops brick-red, and the flowers of 'Silver Gumdrop' are red and not cream. Compared to 'Mocha', the new plant has smaller leaves with intense silvering and that develop blushes of rose, and the flowers are red and not cream. 'Stainless Steel' has white flowers and the foliage has a more brown undertone and less purple. Compared to 'Mocha Mint', the new plant has more rosy blush to the foliage and the flowers are a deeper red. 'Milan' the other male grandparent has more reddish coloration in the foliage and less silver, and the flowers are pink. The nearest similar coral bells is 'Blackberry Ice' U.S. Plant Pat. No. 26,788 which has foliage with burgundy and less silver and has creamy colored flowers and not the red of 'Silver Gumdrop'.

*Heuchera* 'Silver Gumdrop' differs from its parents as well as all other coral bells known to the applicant in the following combined traits:

1. The foliage color is intensely silver foliage with very thin dark green surrounding veins.

2. Foliage develops a complementary rosy blush by mid-summer.
3. Adorned with vibrant pink flowers from early to late summer for nine weeks on burgundy panicles.
4. Leaves are cordate with rounded apices and lobes.
5. The new plant has a compact habit and many small individual leaves.

BRIEF DESCRIPTION OF THE DRAWING

The photograph of the new plant demonstrates the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
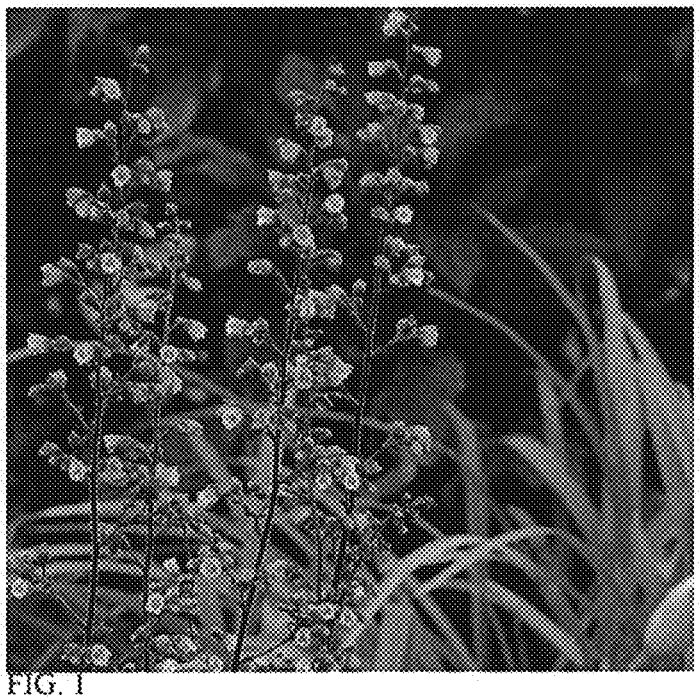
FIG. 1 shows a close-up of the flowers and buds.
Figure 2:
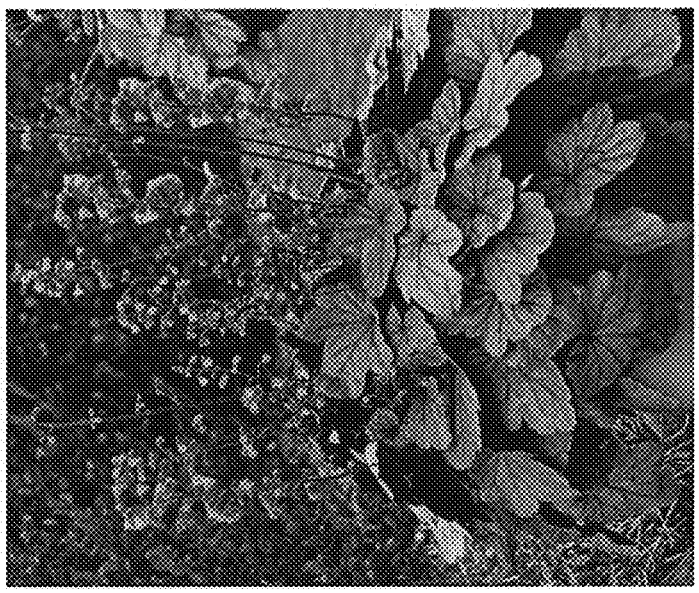
FIG. 2 shows a one-year-old plant in a container just before flowering.

The following description is based on a one-year-old plant growing in a container in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was the proprietary unreleased hybrid known only by the breeder code 12-490-01 (not patented) and the pollen or male parent was a proprietary unreleased hybrid known only by the breeder code K11-52-15.

Plant habit: Hardy herbaceous perennial with compact basal rosette of foliage; mounded foliage about 15.0 cm tall and 35.0 cm in diameter with scapes to about 55 cm long; stems to about 1.5 cm long and 1.0 cm diameter at base with about 15 to 20 leaves per stem and six main stems per plant.

Roots: Fibrous, finely branched.

Growth rate: Rapid, rooting from cutting in two weeks and finishing in three-liter container in about 3 months.

Foliage: Cordate, minutely puberulent adaxial and abaxial; palmately shallowly lobed with five main lobes dissected less than one-third the way to petiole; apex rounded, base cordate to auriculate with basal lobes rarely imbricate; margins crenate to mucronate, hirsutulous; lustrous abaxial and matte adaxial; held nearly horizontal.

Leaf blade size: To about 10.5 cm wide and about 10.0 cm long, average about 10.5 cm wide and about 9.0 cm long.

Leaf color: Spring and young emerging leaves adaxial between RHS N187C and RHS N187B with thin area surrounding veins of nearest N186B, spring and young emerging leaves abaxial nearest RHS 187B; mature mid-season leaves adaxial blend of nearest RHS N187C and RHS N189C thin area surrounding veins of nearest RHS N189A and many leaves picking up a strong blush of a blend between RHS 71A and RHS N186C, abaxial mature mid-season leaves nearest RHS N186C; fall and winter adaxial a blend between RHS 195A and RHS 199D with a blush of nearest RHS N187B, abaxial nearest RHS N186C.

Leaf quantity: Dense, about 100 per plant.

Veins: Palmate, hirsutulous abaxial and adaxial; costate abaxial, slightly impressed adaxial.

Vein color: On emerging or early spring foliage adaxial nearest RHS 186A with emerging or early spring abaxial nearest RHS 187B; mid-season and flowering time adaxial blend between RHS 195A and RHS 186C, mid-season and flowering time abaxial between RHS 191B and RHS 191C.

Petiole: Terete with base amplexicaul; with pubescent hairs to about 2.0 mm long; average about 8.0 cm long and about 2.0 mm diameter above stipule and 10.0 mm at base including stipule.

Petiole color: Emerging leaf blend nearest RHS 187A; mature leaf near base of petiole nearest RHS 194D with stipples of nearest RHS 187B and a dark stripe of nearest RHS 187B on adaxial center, distally nearest RHS 189A with stippling nearest RHS 187B.

Stipule: At base of petiole, about 1.0 cm long and about 1.0 cm wide at base.

Stipule color: Adaxial and abaxial nearest RHS 71A toward longitudinal center and nearest RHS 186C to RHS 186D toward margin.

Peduncle: Panicle; terete; stiff; pubescent; upright; to about 65.0 cm long and 2.5 mm diameter at base, average about 62 cm tall and about 2.0 mm diameter; about fourteen per plant with up to 120 flowers per panicle, average about 90; branched panicle with up to 14 branches up to 4.0 cm long and 1.0 mm diameter decreasing distally, average 12 branches per panicle; branches semi-drooping distally.

Flowering longevity: Panicle effective for about three to four weeks; repeating for about six to nine weeks.

Peduncle color: Young developing nearest RHS 187B, mature nearest RHS 187A.

Pedicel: Terete, finely puberulent, average about 3.0 mm long and 0.5 mm diameter.

Pedicel color: Between RHS 187B and RHS 187B.

Buds one day prior to opening: Globose; rounded apex and attenuate base; puberulent to glandular; about 6.0 mm long and 4.0 mm diameter.

Bud color one day prior to opening: Basal portion between RHS 53A and RHS 53B, becoming nearest RHS 53C in distal one half.

Flower: Perfect, campanulate, actinomorphic, about 7.5 mm long and 6.5 mm in diameter at face; individual flowers lasting about 4 days on plant or as cut flower; three weeks for whole inflorescence and nine weeks with repeat panicles.

Flower attitude: Outward to slightly drooping.

Calyx: Five, apex rounded, base fused in proximal 3.5 mm to form hypanthium; pubescent to glandular abaxial, glabrous adaxial; about 7.5 mm long and 6.5 mm wide.

Calyx color: Abaxial base between RHS 53A and RHS 63B, distally lightening to between RHS 53D and RHS 54A, adaxial distally nearest RHS 55B lightening near base to lighter than RHS 56D.

Petals: Five, oblanceolate to spatulate, acute apex and attenuate base, entire, glabrous abaxial and adaxial, about 5.5 mm long and 1.0 mm wide in middle.

Petal color: Abaxial and adaxial between RHS 56D and RHS N155C.

Androecium: Five adnate to adaxial sepal about 1.0 mm above base.

*Filaments*.—Five, thin, glabrous; about 3.5 mm long and less than 0.3 mm diameter, color white, lighter than RHS 155D.

*Anthers*.—Ellipsoidal, distinct, basifixed, longitudinal; color nearest RHS 181C.

*Pollen*.—Abundant color nearest RHS N25A.

Gynoecium: One, two-beaked; half-inferior; bifid style with pistil split at ovary; 6.0 mm long.

*Style*.—Bifid; split apart at apex of ovary; about 4.5 mm long and about 1.0 mm diameter; color nearest RHS 155D.

*Stigma*.—Rounded apex, about 0.5 mm diameter; color nearest RHS 155D.

*Ovary*.—Half-inferior, about 2.5 mm long and 2.0 mm diameter; ellipsoidal to globose, base rounded; color nearest RHS 150D.

Fruit: Two-beaked capsule, about 5.5 mm long and 3.0 mm diameter at widest portion; color nearest RHS 199A when mature.

Seeds: Linear; about 2.0 mm long; color nearest RHS 202A.

Disease and pest tolerance: The new plant grows best with ample moisture and drainage in either part sun or part shade. Cold hardy from USDA zones 4 to 9. Other resistance and tolerance outside of that normal for coral bells is not known.

It is claimed:

1. The new and distinct coral bells plant named *Heuchera* 'Silver Gumdrop' as herein described and illustrated.

* * * * *